(12) United States Patent
Mosher

(10) Patent No.: US 10,570,357 B2
(45) Date of Patent: Feb. 25, 2020

(54) IN-LINE DETECTION OF CHEMICAL COMPOUNDS IN BEER

(71) Applicant: Michael Mosher, Greeley, CO (US)

(72) Inventor: Michael Mosher, Greeley, CO (US)

(73) Assignee: University of Northern Colorado, Greeley, CO (US)

( * ) Notice: Subject to any disclaimer, the term of this patent is extended or adjusted under 35 U.S.C. 154(b) by 538 days.

(21) Appl. No.: 15/185,844

(22) Filed: Jun. 17, 2016

(65) Prior Publication Data

US 2016/0369214 A1 Dec. 22, 2016

Related U.S. Application Data

(60) Provisional application No. 62/180,865, filed on Jun. 17, 2015.

(51) Int. Cl.
*C12C 11/00* (2006.01)
*G01N 21/3577* (2014.01)
(Continued)

(52) U.S. Cl.
CPC ........ *C12C 11/003* (2013.01); *G01N 21/3577* (2013.01); *G01N 21/552* (2013.01); *G01N 33/146* (2013.01); *G01N 21/65* (2013.01)

(58) Field of Classification Search
CPC .......... C12C 11/003; C12G 1/02; C12G 3/02; C12M 41/48; G01N 21/31; G01N 21/85; G01N 33/14; G01N 2021/3155
(Continued)

(56) References Cited

U.S. PATENT DOCUMENTS

| 4,228,192 A | 10/1980 | Sanden |
| 2013/0275052 A1 | 10/2013 | Loder et al. |

(Continued)

FOREIGN PATENT DOCUMENTS

| CN | 103589550 | 2/2014 |
| CN | 203689080 | 7/2014 |

(Continued)

OTHER PUBLICATIONS

Hough J.S., Briggs D.E., Stevens R., Young T.W. (1982) Chemical and Physical Properties of Beer. In: Malting and Brewing Science. Springer, Boston, MA pp. 776-838.*

(Continued)

*Primary Examiner* — Vera Stulii
(74) *Attorney, Agent, or Firm* — Sheridan Ross P.C.

(57) ABSTRACT

Apparatus, methods, and systems for in-line detection of chemical compounds in beer are provided. In these apparatus, methods, and systems, a small sample of wort is removed from a fermentation vessel, heated, analyzed by infrared attenuated total reflectance (IR-ATR) spectroscopy, and returned to the fermentation vessel. The concentrations of one or more chemical compounds in the wort can be ascertained directly from IR-ATR spectroscopy data, or indirectly from applying an algorithm to the IR-ATR spectroscopy data based on known reaction kinetics and stoichiometry. The apparatus, methods, and systems do not destroy the wort sample or contaminate the fermenting wort and so can be employed continuously during fermentation, and are rapid, accurate, and inexpensive.

11 Claims, 5 Drawing Sheets

(51) Int. Cl.
*G01N 33/14* (2006.01)
*G01N 21/552* (2014.01)
*G01N 21/65* (2006.01)

(58) Field of Classification Search
USPC .................................................. 426/16, 7, 11
See application file for complete search history.

(56) References Cited

U.S. PATENT DOCUMENTS

| | | |
|---|---|---|
| 2014/0073021 A1 | 3/2014 | Bazzana et al. |
| 2014/0160480 A1 | 6/2014 | Imre et al. |
| 2014/0251835 A1 | 9/2014 | Mitchell et al. |

FOREIGN PATENT DOCUMENTS

| | | |
|---|---|---|
| DE | 202004013614 | 11/2004 |
| DE | 102007047175 | 4/2009 |
| EP | 1298197 | 4/2003 |
| EP | 1762837 | 3/2007 |
| EP | 1903329 | 3/2008 |
| GB | 2018423 | 10/1979 |
| WO | WO 2014/087374 | 6/2014 |
| WO | WO 2015/032551 | 3/2015 |
| WO | WO 2015/155353 | 10/2015 |
| WO | WO 2017218039 A1 * | 12/2017 |

OTHER PUBLICATIONS

International Search Report and Written Opinion for International (PCT) Patent Application No. PCT/US2016/66441, dated Feb. 9, 2017.

* cited by examiner

IN-LINE DETECTION OF CHEMICAL COMPOUNDS IN BEER

CROSS-REFERENCE TO RELATED APPLICATION

This application claims the benefit of U.S. Provisional Patent Application No. 62/180,865 entitled "In-Line Detection of Chemical Compounds in Beer" filed on Jun. 17, 2015, the entire disclosure of which is incorporated herein by reference.

FIELD OF THE INVENTION

This disclosure relates to apparatus, methods, and systems for detecting carbon dioxide levels in aqueous samples, and particularly for measuring carbon dioxide levels in beer both before and after microwave heating of a sample.

BACKGROUND OF THE PRESENT INVENTION

One of the first steps in the brewing of beer is a process known as "mashing," in which a mix of milled grain, typically all or mostly malted barley, is combined with water and the resulting mixture is heated. The liquid extracted from the mashing process, known as "wort," is then placed in a fermenter, where brewing yeast converts the sugars in the wort to ethanol. In the initial stages of fermentation, the yeast cells reproduce rapidly and produce excess quantities of α-acetolactate (AAL), which then undergoes a decarboxylation reaction to produce butane-2,3-dione, known to brewers as "diacetyl," and carbon dioxide. If fermentation is allowed to proceed long enough for the yeast's primary food source, i.e. the sugars in the wort, to become scarce, the yeast will slowly reabsorb the diacetyl.

Diacetyl has a very distinctive and intense buttery flavor. In some styles of beer, a buttery flavor can be part of the intended flavor profile and low to moderate levels of diacetyl are considered acceptable or even desirable; in many other styles, however, butter is considered an "off" flavor and the presence of diacetyl is considered a serious flaw in the beer. Elevated diacetyl levels can also indicate bacterial contamination of brewing equipment. Monitoring the concentration of diacetyl in the beer is thus necessary for control of the fermentation process and so is of paramount importance to the brewer.

Methods for monitoring the diacetyl level in beer which have previously been known and described in the art have generally utilized either gas chromatography (GC) or field asymmetric ion mobility spectrometry (FAIMS). To be most effective, these processes often require samples of the beer to be processed and loaded, and many breweries, especially smaller ones, frequently opt to send samples to third-party laboratories for analysis. As a result, measuring diacetyl levels in the beer can often be quite time-consuming, which can subject the wort to a longer fermentation time than the brewer would consider optimal. In addition, these methods typically require that diacetyl measurements be taken at discrete times during fermentation, rather than allowing the brewer to monitor diacetyl levels in the beer more continuously throughout fermentation.

Many technologies for monitoring the beer fermentation process have previously been known and described in the art, but each has a significant drawback and/or a lack of an important and useful functionality. For example, PCT Application Publication No. 2015/032551, entitled "Method and apparatus for beer fermentation," published 12 Mar. 2015 to Nordkvist et al. ("Nordkvist"), describes a method for beer fermentation, comprising the steps of inserting wort and yeast into a vessel to initiate a fermentation process, the wort and yeast forming a vessel content; measuring, with an online measuring device, a first extract value that is representative of an extract level of the vessel content; and automatically controlling a mixing device, dependent on the first extract value, to withdraw vessel content from the vessel and re-inject it into the vessel for effecting mixing of the vessel content. The method monitors and controls the beer fermentation process by using an on-line measuring device.

European Patent Application Publication No. 1,298,197, entitled "Method and apparatus for treating mash," published 2 Apr. 2003 to Nowrouzi ("Nowrouzi"), describes a brewing process in a closed fermentation vat with a mash charge, comprising generating a gas containing carbon dioxide, wherein a measured carbon dioxide value is used as a temperature control parameter.

IR-ATR measurements have been used for the assessment of the concentration of $CO_2$ in a liquid. For example, European Patent No. 1,903,329, entitled "An apparatus and method for optically determining the presence of carbon dioxide," issued 22 Dec. 2010 to Tavernier et al. ("Tavernier"), describes an apparatus for optically determining the presence of carbon dioxide within a fluid.

There is a long-felt need for in-line methods of monitoring diacetyl concentration in beer during fermentation that are sufficiently robust and sensitive to enable precise control over fermentation and thereby improve the efficiency of the brewing process and the consistency and quality of the beer produced. It is further advantageous that such methods be rapid, accurate, and inexpensive, or at least significantly less costly than laboratory analysis. It would be desirable that these methods do not destroy the beer sampled or contaminate the fermenting wort.

BRIEF SUMMARY OF CERTAIN EMBODIMENTS OF THE INVENTION

Certain embodiments include an in-line apparatus for the detection of at least one chemical compound in beer, comprising a wort inlet; a pump, in fluid communication with the wort inlet; a heater, in fluid communication with the pump; an infrared attenuated total reflectance (IR-ATR) cell, in fluid communication with the heater; a wort outlet, in fluid communication with the IR-ATR cell; a controller, interconnected to the pump, the heater, and the IR-ATR cell; and a readout, interconnected to the controller.

In some embodiments, the apparatus further comprises a temperature feedback, interconnected to the heater.

In other embodiments, the at least one chemical compound comprises one or more of α-acetolactate (AAL), butane-2,3-dione ("diacetyl"), carbon dioxide, α-acetohydroxybutyrate, and pentane-2,3-dione.

In other embodiments, the infrared attenuated total reflectance (IR-ATR) cell comprises the use of RAMAN spectroscopy, gas electrode analysis, headspace analysis by gas chromatography, or electrochemical detection.

The present disclosure also provides an in-line method for the detection of at least one chemical compound in beer, comprising removing a wort sample from a fermentation vessel, measuring a first carbon dioxide concentration in the wort sample, heating the wort sample, obtaining spectroscopy data for the wort sample by infrared attenuated total reflectance (IR-ATR) spectroscopy, interpreting the spectroscopy data according to a first algorithm to determine a second carbon dioxide concentration in the wort sample, calculating a concentration of the at least one chemical compound in the wort sample according to the second carbon dioxide concentration and a second algorithm, and returning the wort sample to the fermentation vessel.

In many embodiments, the at least one chemical compound comprises one or more of α-acetolactate, butane-2,3-dione, carbon dioxide, α-acetohydroxybutyrate, and pentane-2,3-dione.

In some embodiments, the method may be completed in a time of between about 30 seconds and about 6 minutes. In a preferred embodiment, the method is completed in a time of between about 2 minutes and about 3 minutes.

The present disclosure further provides an in-line system for the detection of at least one chemical compound in beer, comprising a wort inlet, receiving a wort sample from a fermentation vessel; a pump, receiving the wort sample from the wort inlet and pumping the wort sample through a pump outlet; a heater, receiving the wort sample from the pump via the pump outlet and heating the wort sample; an infrared attenuated total reflectance (IR-ATR) cell, receiving the wort sample from the heater and generating spectroscopy data; a wort outlet, receiving the wort sample from the IR-ATR cell and returning the wort sample to the fermentation vessel; a controller, interconnected to the pump, the heater, and the IR-ATR cell, controlling a flow rate of the wort sample through the pump outlet, controlling a power of the heater, receiving the spectroscopy data from the IR-ATR cell, and interpreting the spectroscopy data according to an algorithm to determine a concentration in the wort sample of the at least one chemical compound; and a readout, interconnected to the controller and displaying the concentration in the wort sample of the at least one chemical compound.

In certain embodiments, the system further comprises a temperature feedback, interconnected to the heater and displaying the temperature within the heater of the wort sample.

In some embodiments, the at least one chemical compound comprises one or more of α-acetolactate, butane-2,3-dione, carbon dioxide, α-acetohydroxybutyrate, and pentane-2,3-dione.

The present disclosure still further provides a method for limiting the quantity of at least one chemical compound produced by a beer brewing process, comprising the steps of providing a system, comprising a heater, an infrared attenuated total reflectance (IR-ATR) cell in fluid communication with the heater, and a controller interconnected to the pump, the heater, the IR-ATR cell, and a fermentation vessel; removing a wort sample from the fermentation vessel; measuring a first carbon dioxide concentration in the wort sample; heating the wort sample; obtaining spectroscopy data for the wort sample by IR-ATR spectroscopy; interpreting the spectroscopy data according to the first carbon dioxide concentration and a first algorithm to determine a second carbon dioxide concentration in the wort sample; calculating a concentration of the diacetyl compounds in the wort sample according to the second carbon dioxide concentration and a second algorithm; returning the wort sample to the fermentation vessel; and modifying at least one fermentation parameter of the beer brewing process according to the concentration of the diacetyl compounds and a third algorithm.

In some embodiments, the at least one chemical compound comprises at least one vicinal diketone (VDK).

In some embodiments, the heater is a microwave heater.

In some embodiments, the at least one fermentation parameter comprises one or more of a fermentation time and a fermentation temperature.

In some embodiments, light emitted by and reflected in the IR-ATR cell may have an emitted wavelength of between about 1 micron and about 100 microns.

In some embodiments, the wort sample may have a mass of between about 0.01 g and about 0.5 g. In other embodiments, the wort sample may have a volume of between about 0.01 mL and about 0.5 mL.

In some embodiments, the wort sample is heated to a temperature sufficient to rapidly convert substantially all of the AAL in the wort sample to VDKs and carbon dioxide. By way of non-limiting example, the temperature to which the wort sample is heated may be between about 50° C. and about 110° C., or may be at least about 35° C.

The advantages of the present invention will be apparent from the disclosure contained herein.

For purposes of further disclosure and to comply with applicable written description and enablement requirements, the following references generally relate to apparatus, methods, and systems for measuring or sensing VDKs, such as diacetyl, or their precursors in beer, and related apparatus, methods, and systems, and are hereby incorporated by reference in their entireties:

British Patent Application Publication No. 2,018,423, entitled "Determination of the constituents of beer or beer wort using infrared absorption," published 17 Oct. 1979 to Sanden ("Sanden"). Sanden describes a method by which beer and/or beer wort components are determined quantitatively by transmitting IR light through the beer. The IR absorption is measured and evaluated at specific wavelengths of 2.9-3.1μ for the alcohol component, 9.6-9.8μ for the extract or wort, and 4.2-4.4μ for $CO_2$. The proportions of alcohol, extract or wort, and dissolved $CO_2$ can be determined individually and accurately. IR absorption is independent of external conditions. Direct readings can be obtained without specific monitoring instruments.

European Patent Application Publication No. 1,298,197, entitled "Method and apparatus for treating mash," published 2 Apr. 2003 to Nowrouzi ("Nowrouzi"). Nowrouzi describes a brewing process in a closed fermentation vat with a mash charge, comprising generating a gas containing carbon dioxide, wherein a measured carbon dioxide value is used as a temperature control parameter.

German Utility Model No. 20/2004/013614, entitled "Sensor for spectrometric determination of e.g. carbon dioxide in drinks industry has housing containing radiation source and two detectors, front of housing consisting of inert inner insert and outer polymer matrix," granted 18 Nov. 2004 and assigned to Mettler-Toledo GmbH ("Mettler-Toledo"). Mettler-Toledo describes a sensor for spectrometric determination of components, especially carbon dioxide, dissolved in a liquid, the sensor having a housing containing a radiation source and two detectors. The front of the housing forms an optical element and consists of an inert inner insert and an outer polymer matrix.

German Patent Application Publication No. 10/2007/047175, entitled "Monitoring fermenting process in fermenting container, comprises colorimetrically determining flow rate of gas escaping from the container, and determining the fermenting progress, residual sugar, carbon dioxide content or alcohol content," published 9 Apr. 2009 to Hoerner ("Hoerner"). Hoerner describes a method for monitoring a fermenting process in a fermenting container, comprising colorimetrically determining a flow rate of the gas escaping from the container, measuring temperature and the direction of flow of the gas and the level of liquid in a fermenting tube, and determining the fermenting progress, residual sugar, carbon dioxide content or the alcohol content by the measured values and/or determined data.

U.S. Patent Application Publication No. 2013/0275052, entitled "Method and device of determining a CO2 content in a liquid," published 17 Oct. 2013 to Loder et al. ("Loder"). Loder describes a method whereby three absorption measurements of the liquid are carried out, respectively, at a wavelength within a first wavelength range between 4200 and 4300 nm to measure a first absorption value with attenuated total reflectance, at a second wavelength within a second wavelength range between 3590 and 4050 nm and a second absorption value with attenuated total reflectance, and at a third wavelength within a third wavelength range between 3300 and 3900 nm and a third absorption value with attenuated total reflectance. A pre-defined model function is used for determining the $CO_2$ content based on the first, second, and third absorption values.

European Patent Application Publication No. 1,762,837, entitled "Method and measuring device for determining the CO2 concentration in a CO2-containing liquid," published 18 Dec. 2013 to Martynowicz et al. ("Martynowicz"). Martynowicz describes a method for determining the $CO_2$ concentration in a $CO_2$-containing liquid, in particular $CO_2$-containing soft drinks, the method characterized by the steps of a) providing a predetermined amount of $CO_2$-containing liquid with a predetermined volume of head gas that is in gas equilibrium with the liquid; b) determining the total pressure of the head gas; c) determining the partial pressure of oxygen ($O_2$) of the head gas; d) determining the partial pressure of nitrogen ($N_2$) of the head gas; e) deriving the partial pressure of carbon dioxide ($CO_2$) of the head gas from the total pressure and the partial pressures of oxygen and nitrogen; and f) deriving the $CO_2$ concentration in the $CO_2$-containing liquid from the derived partial pressure of carbon dioxide.

Chinese Patent Application Publication No. 103589550, entitled "Carbon dioxide balanced system for beer brewing technology," published 19 Feb. 2014 to Yi et al. ("Yi"). Yi describes a carbon dioxide balanced system for a beer brewing technology, comprising a carbon dioxide recovery system, a fermentation tank, a bright beer tank, pressure reduction and filtration devices, automatic regulating valves, and pressure sensors, wherein an outlet of the carbon dioxide recovery system is connected with the bright beer tank sequentially through the first pressure reduction and filtration device and the first automatic regulating valve and is also connected with the fermentation tank sequentially through the second pressure reduction and filtration device and the second automatic regulating valve, the bright beer tank and the fermentation tank are connected together through the first pressure sensor and the third automatic regulating valve, and the fermentation tank and the carbon dioxide recovery system are connected together through the second pressure sensor and the fourth automatic regulating valve and are also connected with a recovery system pipeline in parallel.

PCT Application Publication No. 2014/087374, entitled "Monitoring method and probe of alcoholic fermentation with UV-VIS-SWNIR spectroscopy," published 12 Jun. 2014 to Martins et al. ("Martins"). Martins describes a universal method and probe for the monitoring of beer quality during fermentation, through the use of UV-VIS-SWNIR (ultraviolet/visible/short-wave near-infrared) spectroscopy.

U.S. Patent Application Publication No. 2014/0160480, entitled "Method and sensor device for measuring a carbon dioxide content in a fluid," published 12 Jun. 2014 to Imre et al. ("Imre"). Imre describes an ATR sensor having a housing and sensor components in the housing, including an electromagnetic radiation source for emitting a predefined wavelength range, a reflection body permeable for radiation and contactable with a fluid to be evaluated, and a detector for the reflected radiation, as well as other members for conducting the measurement and for operation. The sensor is particularly suited for measuring a $CO_2$ content of a fluid.

Chinese Utility Model No. 203689080, entitled "Beer fermentation tank monitoring system," granted 2 Jul. 2014 to Hou ("Hou"). Hou describes a beer fermentation tank monitoring system including a controller; a paperless recorder; a sensor unit, including a temperature sensor, a carbon dioxide concentration sensor, a gas flow sensor, a liquid flow sensor, and a microbial sensor; and a data collection and processing device, processing data collected by the sensor unit and sending control instructions to the controller according to the processed data, the data collection and processing device including a shell and a circuit board, the circuit board provided with a microprocessor, a power module, a multi-channel signal conversion board, a data acquisition card, a decoder, a display diving circuit, an encoder, a watchdog circuit, an EEPROM storage, an I/O extension interface, and an alarm driving circuit.

PCT Application Publication No. 2015/032551, entitled "Method and apparatus for beer fermentation," published 12 Mar. 2015 to Nordkvist et al. ("Nordkvist"). Nordkvist describes a method for beer fermentation, comprising the steps of inserting wort and yeast into a vessel to initiate a fermentation process, the wort and yeast forming a vessel content; measuring, with an online measuring device, a first extract value that is representative of an extract level of the vessel content; and automatically controlling a mixing device, dependent on the first extract value, to withdraw vessel content from the vessel and re-inject it into the vessel for effecting mixing of the vessel content. The method monitors and controls the beer fermentation process by using an on-line measuring device.

Unlike the prior art, the present invention, in various embodiments, employs a method of heating, preferably microwave heating, and an analysis of carbon dioxide levels in a small (e.g. between about 0.01 mL and 0.5 mL) sample of beer, employing an IR-ATR cell, in order to measure AAL levels during the fermentation of the beer.

Methods, systems, and devices of the present invention include in-line monitoring of the lactate level of a beer fermentation process, the method employing an in-line IR-ATR spectroscopic technique to assess the level of $CO_2$ as the measure of AAL quantity in beer samples. The methods, systems, and devices may be initiated and/or controlled by a human user, or they may be at least partially automated and/or computer-controlled.

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

DETAILED DESCRIPTION OF CERTAIN EMBODIMENTS OF THE INVENTION

Unless defined otherwise, all technical and scientific terms used herein have the same meaning as is commonly understood by one of ordinary skill in the art. All patents, applications, published applications, and other publications to which reference is made herein are incorporated by reference in their entirety. In the event that there is a plurality of definitions for a term herein, the definition provided in the Brief Summary of Certain Embodiments of the Invention prevails unless otherwise stated.

Figure 1A:
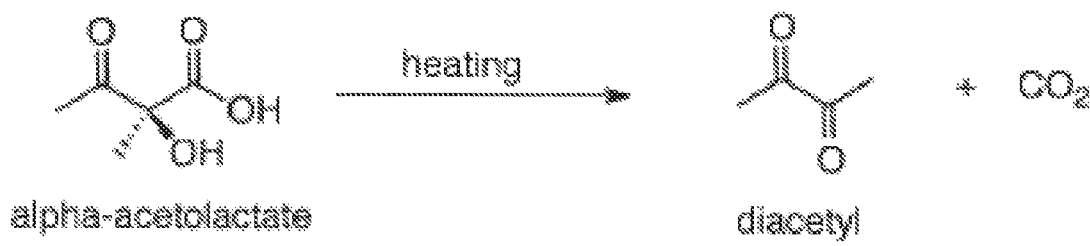
FIG. 1A is an illustration of a decarboxylation reaction that takes place during the fermentation step of the process for brewing beer.

Referring now to FIG. 1A, the chemical structure of α-acetolactate (AAL) is illustrated. During the fermentation step of the process for brewing beer, brewing yeast consumes the sugars in the wort and produces, in addition to ethanol, AAL. Throughout the course of the fermentation, the AAL undergoes a decarboxylation reaction to form butane-2,3-dione ("diacetyl") and carbon dioxide; as illustrated in FIG. 1A, heating drives the reaction equilibrium to the right, i.e. toward the decarboxylation products, diacetyl and carbon dioxide. Thus, lower temperatures in the fermentation vessel result in higher levels of AAL and lower levels of diacetyl and carbon dioxide, and higher temperatures in the fermentation vessel result in lower levels of AAL and higher levels of diacetyl and carbon dioxide.

At an intermediate point in the fermentation process, the brewing yeast's primary source of food, i.e. the sugars in the wort, become scarce, and the yeast begin to reabsorb the diacetyl. Those of ordinary skill in the art of brewing understand that the yeast's reabsorption of the diacetyl is strongly dependent on temperature, and that "aging" a beer for a sufficiently long time will cause the brewing yeast to reabsorb substantially all of the diacetyl in the beer. In particular, it is well-known to brewers that substantially complete reabsorption of diacetyl typically takes about two weeks of aging in ales but at least about four weeks of aging in lagers, which are usually fermented and aged at lower temperatures than ales. However, as discussed above in the Description of the Related Art, it is generally difficult for brewers to have accurate and precise knowledge of the levels of AAL, diacetyl, or carbon dioxide at any given moment during the fermentation and aging processes.

The reaction kinetics of the decarboxylation of AAL to form diacetyl and carbon dioxide are well-known, particularly with regard to the reaction's temperature dependence. It is also well-known that, stoichiometrically, the reaction of one molecule of AAL will form one molecule of diacetyl and one molecule of carbon dioxide, as illustrated in FIG. 1A. It is thus possible to calculate the level of any one of the decarboxylation reaction compounds (AAL, diacetyl, carbon dioxide) if the level, and/or the change in the level with temperature, of another of the decarboxylation reaction compounds is known. By way of non-limiting example, a brewer may measure the concentration in a sample of wort/beer of carbon dioxide at the fermentation temperature, and at a significantly higher temperature. The higher temperature may be selected such that all of the AAL in the sample is rapidly converted to diacetyl and carbon dioxide. The brewer, knowing the decarboxylation reaction kinetics and stoichiometry and the rate at which the brewing yeast reabsorbs diacetyl, can then compute the concentration in the wort/beer of AAL based on the difference between the two carbon dioxide measurements.

Figure 1B:
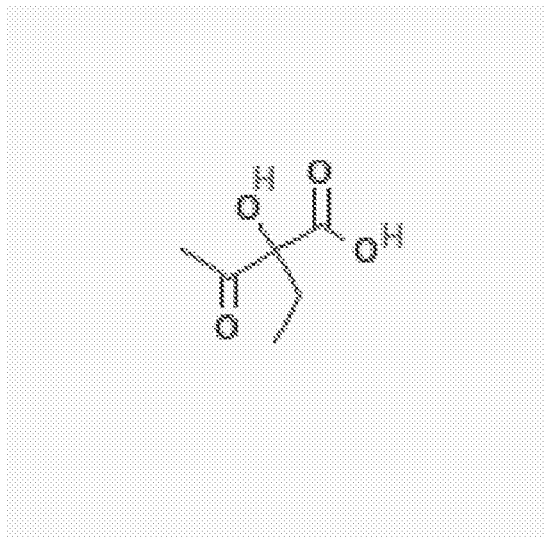
FIGS. 1B and 1C are illustrations of secondary products of the decarboxylation reaction illustrated in FIG. 1A.
Figure 1C:
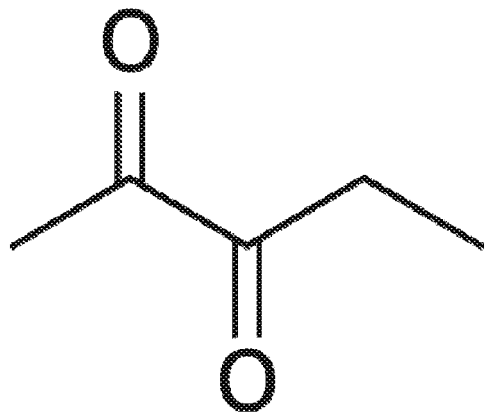

Referring now to FIGS. 1B and 1C, the chemical structures of secondary products of the decarboxylation reaction illustrated in FIG. 1A are illustrated. Specifically, FIG. 1B illustrates the chemical structure of α-acetohydroxybutyrate, and FIG. 1C illustrates the chemical structure of pentane-2,3-dione. Each of these compounds may be produced during the fermentation step and contribute to the total concentration of VDKs in the beer.

Figure 2:
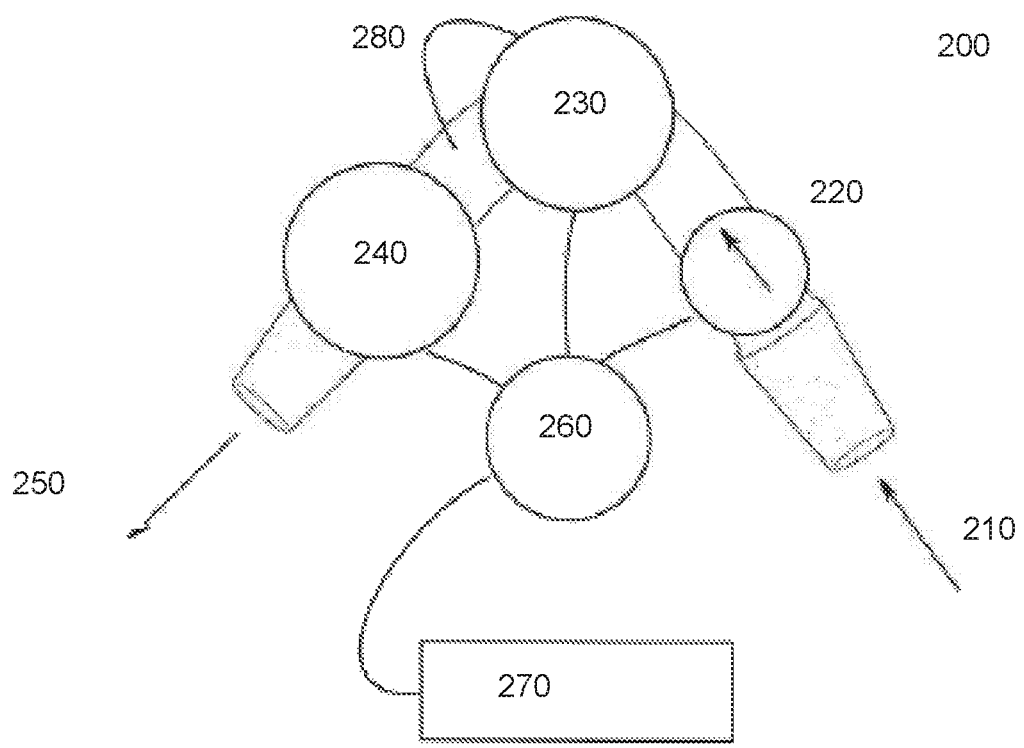
FIG. 2 is a schematic diagram of an in-line system for the detection of chemical compounds in beer, according to embodiments of the present disclosure.

Referring now to FIG. 2, an in-line system 200 for the detection of at least one chemical compound in beer comprises a wort inlet 210, receiving a wort sample from a fermentation vessel; a peristaltic pump 220, receiving the wort sample from the wort inlet 210 and pumping the wort sample through a peristaltic pump outlet; a microwave heater 230, receiving the wort sample from the peristaltic pump 220 via the peristaltic pump outlet and heating the wort sample; an infrared attenuated total reflectance (IR-ATR) cell 240, receiving the wort sample from the microwave heater 230 and generating spectroscopy data; a wort outlet 250, receiving the wort sample from the IR-ATR cell 240 and returning the wort sample to the fermentation vessel; a controller 260, interconnected to the peristaltic pump 220, the microwave heater 230, and the IR-ATR cell 240, controlling a flow rate of the wort sample through the peristaltic pump outlet, controlling a power of the microwave heater 230, receiving the spectroscopy data from the IR-ATR cell 240, and interpreting the spectroscopy data according to an algorithm to determine a concentration in the wort sample of the at least one chemical compound; and a readout 270, interconnected to the controller 260 and displaying the concentration in the wort sample of the at least one chemical compound. In the embodiment illustrated in FIG. 2, the system 200 further comprises a temperature feedback 280, interconnected to the microwave heater 230 and displaying the temperature within the microwave heater 230 of the wort sample.

In the embodiment illustrated in FIG. 2, the system 200 is configured to measure the concentration in the wort sample of carbon dioxide at two different temperatures, and the controller 260 uses the two carbon dioxide measurements to calculate the concentrations in the wort sample of AAL and diacetyl. At certain times during operation of the system 200, the microwave heater 230 does not operate, and the IR-ATR cell 240 thus obtains spectroscopy data corresponding to the wort at the fermentation temperature. The controller 260 utilizes this spectroscopy data to ascertain a "background" level of carbon dioxide, i.e. the concentration of carbon dioxide present in the wort in the fermentation vessel. Then, the microwave heater 230 is activated and heats another sample of wort from the fermentation vessel to a temperature high enough to rapidly convert substantially all of the AAL in the wort sample to diacetyl and carbon dioxide; the temperature feedback 280 enables a user of the system 200, particularly a brewer, to ensure that the temperature of the wort sample in the microwave heater 230 is sufficiently high. The IR-ATR cell 240 then obtains spectroscopy data corresponding to the fully-converted wort; the controller 260 may utilize this spectroscopy data to ascertain the "converted" level of carbon dioxide, i.e. the concentration of carbon dioxide present in the wort after conversion of substantially all of the AAL. Because AAL is converted to carbon dioxide in a molecular ratio of 1:1, as illustrated in FIG. 1A, the difference between the two carbon dioxide measurements will be equal, in terms of number of molecules, to the concentration of AAL in the wort in the fermentation vessel. Because the rate of diacetyl reuptake by the brewing yeast in the fermentation vessel is well-known to those of skill in the art, the controller 260 can convert this calculated AAL concentration, via an algorithm, to the concentration of diacetyl in the wort. The readout 270 can be configured to display any combination of the carbon dioxide concentration, the AAL concentration, and the diacetyl concentration, as determined by the controller 260. In addition, the user can adjust the power of the microwave heater 230, and thus the temperature of the wort sample in the microwave heater 230, via the controller 260.

Figure 3:
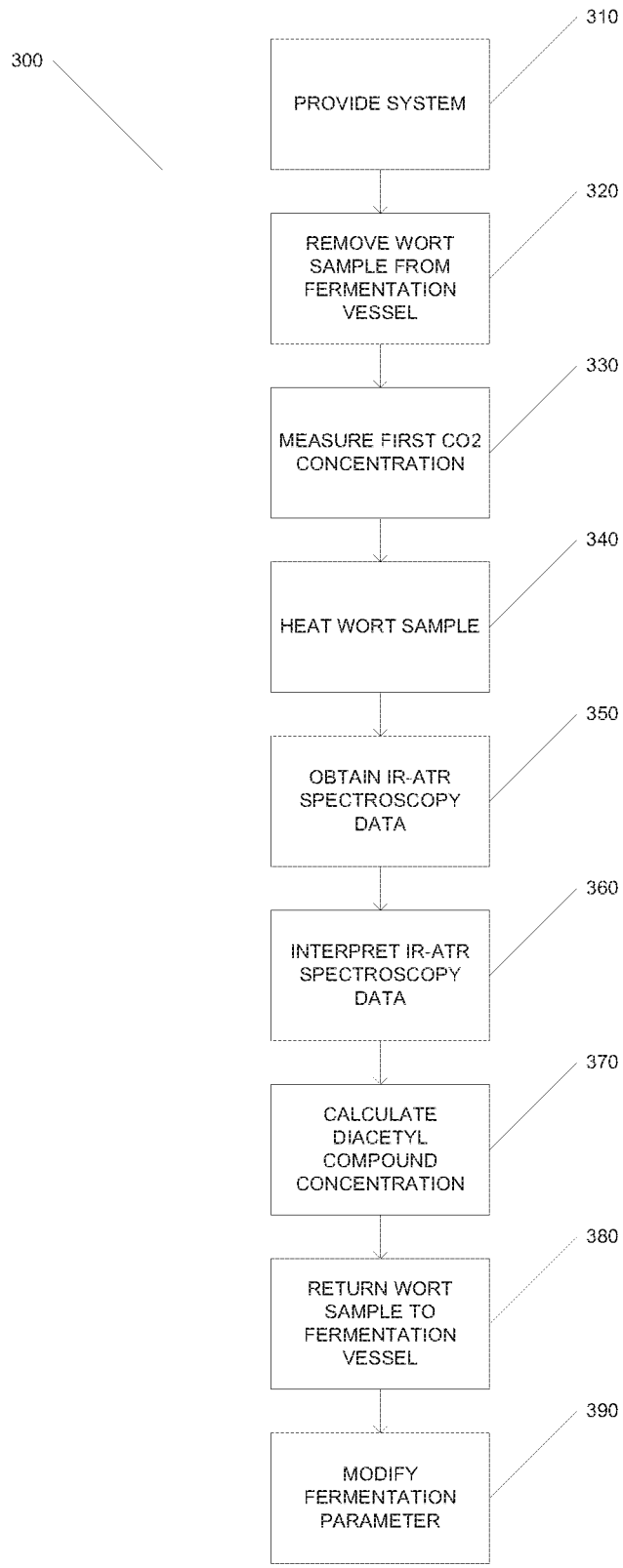
FIG. 3 is a flow chart illustrating a method of limiting the quantity of diacetyl compounds produced by a beer brewing process, according to embodiments of the present disclosure.

Referring now to FIG. 3, a method 300 of limiting the quantity of diacetyl compounds produced in a beer brewing process is illustrated. In providing step 310, a system is provided, the system comprising a heater; an infrared attenuated total reflectance (IR-ATR) cell, in fluid communication with the heater; and a controller, interconnected to the pump, the heater, the IR-ATR cell, and a fermentation vessel; in some embodiments, by way of non-limiting example, the system may be similar to the system illustrated in FIG. 2. In removing step 320, a wort sample is removed from the fermentation vessel. In measuring step 330, a first carbon dioxide concentration in the wort sample is measured; in some embodiments, by way of non-limiting example, the first carbon dioxide concentration may be measured by IR-ATR spectroscopy. In heating step 340, the wort sample is heated; in some embodiments, by way of non-limiting example, the temperature to which the wort sample is heated may be sufficient to rapidly convert substantially all of the AAL in the wort sample to diacetyl and carbon dioxide. In obtaining step 350, spectroscopy data for the wort sample are obtained by IR-ATR spectroscopy. In interpreting step 360, the spectroscopy data are interpreted according to a first algorithm to determine a second carbon dioxide concentration in the wort sample. In calculating step 370, a concentration of the diacetyl compounds in the wort sample is calculated according to the second carbon dioxide concentration and a second algorithm. In returning step 380, the wort sample is returned to the fermentation vessel. In modifying step 390, at least one fermentation parameter of the brewing process is modified according to the concentration of the diacetyl compounds and a third algorithm; in some embodiments, by way of non-limiting example, the at least one fermentation parameter may comprise one or more of a fermentation time and a fermentation temperature.

Thus, one aspect of the various embodiments employs a microwave heater and an IR-ATR cell in the monitoring of AAL levels. Nordkvist does not propose using microwave heating or an infrared attenuated total reflectance (IR-ATR) cell for the analysis of $CO_2$ levels in a small beer sample as the measure of the AAL level. In other embodiments, a system may include an apparatus comprising a light emitting source, an optical sensing probe in contact with the fluid to analyze, optical light transmitting means in order to convey the light emitted from the light emitting source to the optical sensing probe and the light reflected by the optical sensing probe to means to discriminate between wavelengths of light beams reflected by the optical sensing probe, and means to convert wavelength-discriminated light beams into measurement data indicating the presence of carbon dioxide within beer, preferably with an optical sensing probe comprising an attenuated total reflection (ATR) absorber. Various embodiments include a method of in-line monitoring of the lactate level of a beer fermentation process, the method employing an in-line IR-ATR spectroscopic technique to assess the level of $CO_2$ as the measure of AAL quantity in beer samples.

Although the embodiment illustrated in FIG. 3 utilizes IR-ATR spectroscopy, it may be understood by those of ordinary skill in the art that other measuring or sensing methods may be suitable for use with other embodiments of the apparatus, methods, and systems disclosed herein. By way of non-limiting example, other embodiments may employ RAMAN spectroscopy, gas electrode analysis, headspace analysis by gas chromatography, or electrochemical detection.

Figure 4:
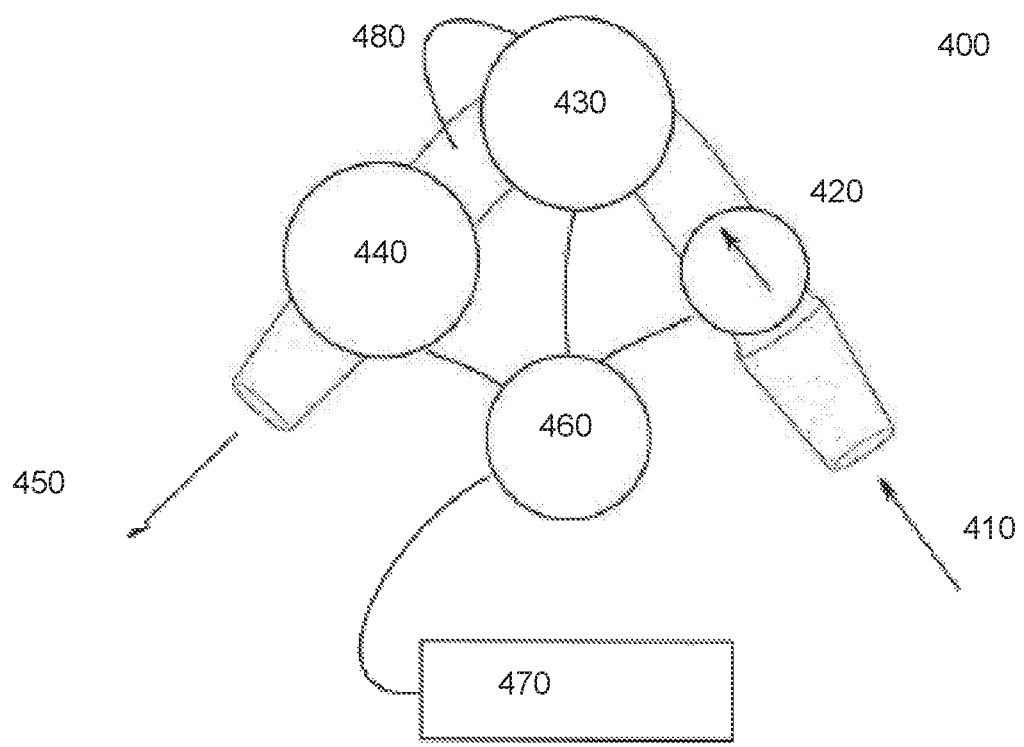
FIG. 4 is a schematic diagram of an in-line system for the detection of carbon dioxide levels in beer, according to embodiments of the present disclosure.
Figure 5:
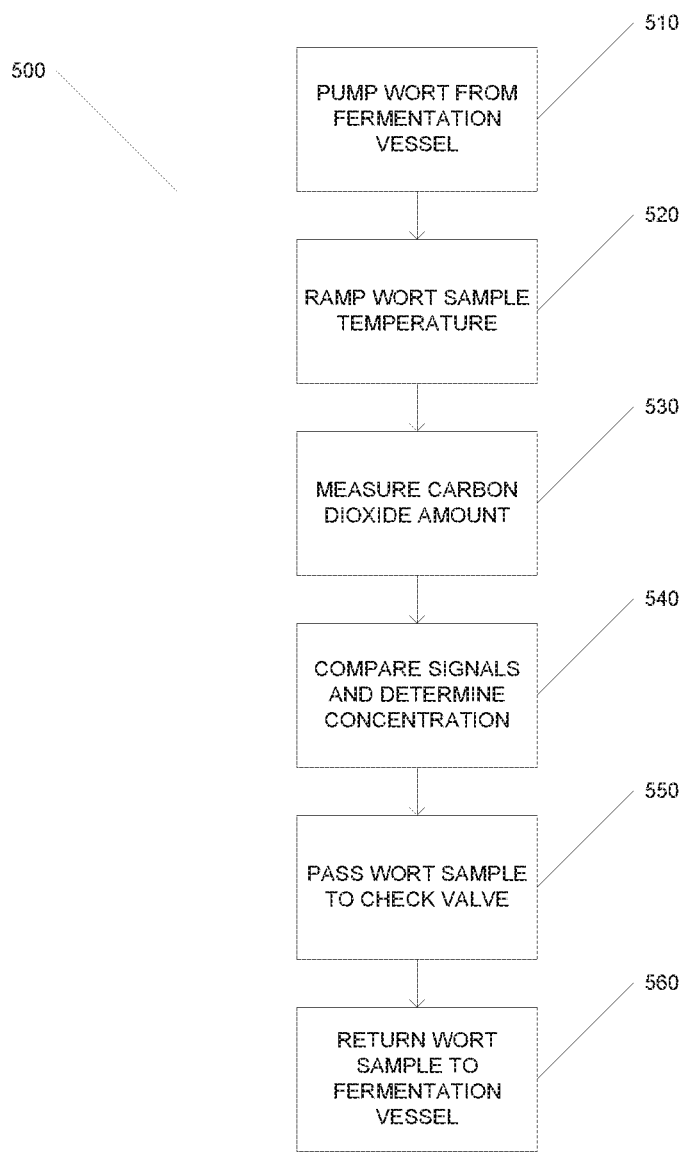
FIG. 5 is a flow chart illustrating an in-line method of determining the carbon dioxide content of beer, according to embodiments of the present disclosure.

Referring now to FIGS. 4 and 5, an in-line system 400 for the detection of carbon dioxide in beer comprises a wort inlet 410, receiving a wort sample from a fermentation vessel; a peristaltic pump 420, receiving the wort sample from the wort inlet 410 and pumping the wort sample through a peristaltic pump outlet; a Peltier heater 430, receiving the wort sample from the peristaltic pump 420 via the peristaltic pump outlet and heating and then cooling the wort sample; an infrared (IR) cell 440, receiving the wort sample from the Peltier heater 430 and generating spectroscopy data; a wort outlet 450, receiving the wort sample from the IR cell 440 and returning the wort sample to the fermentation vessel; a controller 460, interconnected to the peristaltic pump 420, the Peltier heater 430, and the IR cell 440, controlling a flow rate of the wort sample through the peristaltic pump outlet, controlling a power of the Peltier heater 430, receiving the spectroscopy data from the IR cell 440, and interpreting the spectroscopy data according to an algorithm to determine a concentration in the wort sample of carbon dioxide; and a readout 470, interconnected to the controller 460 and displaying the concentration in the wort sample of carbon dioxide. In the embodiment illustrated in FIG. 4, the system 400 further comprises a temperature feedback 480, interconnected to the Peltier heater 430 and displaying the temperature within the Peltier heater 430 of the wort sample. The system 400 may further comprise a check valve (not illustrated) disposed between the IR cell 440 and the wort outlet 450, which may be used to maintain fluid pressure within the system, eliminate back flow, and avoid degassing of the wort sample during heating.

In the embodiment illustrated in FIG. 4, the peristaltic pump 420 pumps a wort sample into the system 400 from a fermentation vessel, thereby increasing the pressure on the liquid. The wort sample then enters the Peltier heater 430, where it is heated to a decomposition temperature and then cooled back to its initial temperature. The wort sample then enters the IR cell 440, which generates signals that are communicated to the controller 460; the controller 460, according to an algorithm, interprets and compares the signals generated by the IR cell 440 both with the Peltier heater 430 off and with the Peltier heater 430 on to determine a concentration of dissolved carbon dioxide in the wort sample. The wort outlet 450 then returns the wort sample to the fermentation vessel.

The system 400 illustrated in FIG. 4 may be used to implement the method 500 illustrated in FIG. 5. In pumping step 510, a sample of wort is pumped from a fermentation vessel into a Peltier heater by a small pump that increases the pressure on the liquid. In ramping step 520, the wort sample is ramped from a starting temperature up to a decomposition temperature, then back down to the starting temperature. In measuring step 530, the wort sample enters an infrared (IR) cell and the amount of dissolved carbon dioxide in the wort sample is measured by IR spectroscopy. In determining step 540, a controller compares signals from the IR cell when the Peltier heater is off and when the Peltier heater is on to determine the concentration of carbon dioxide in the wort sample. In check valve step 550, the wort sample enters a check valve, which is used to maintain liquid pressure within the system, eliminate back flow, and avoid degassing the wort sample during heating. In returning step 560, the wort sample is returned to the fermentation vessel.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of Certain Embodiments of the Invention, for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of Certain Embodiments of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A method for controlling the quantity of at least one chemical compound in a beer brewing process, comprising the steps of:
   a) providing a system comprising:
      a heater;
      an infrared (IR) cell, in fluid communication with the heater; and
      a controller, interconnected to the pump, the heater, the IR cell, and a fermentation vessel;
   b) removing a wort sample from the fermentation vessel;
   c) measuring a first carbon dioxide concentration in the wort sample;
   d) heating the wort sample to a target temperature;
   e) obtaining spectroscopy data for the wort sample by IR spectroscopy;
   f) interpreting the spectroscopy data according to the first carbon dioxide concentration and a first algorithm to determine a second carbon dioxide concentration in the wort sample;
   g) calculating a concentration of the at least one chemical compound in the wort sample according to the second carbon dioxide concentration and a second algorithm;
   h) returning the wort sample to the fermentation vessel; and
   i) modifying at least one fermentation parameter of the beer brewing process according to the concentration of the at least one chemical compound and a third algorithm, wherein the at least one chemical compound is one or both of α-acetolactate and butane-2,3-dione.

2. The method of claim 1, wherein the method is completed in a time of between about 30 seconds and about 6 minutes.

3. The method of claim 2, wherein the method is completed in a time of between about 2 minutes and about 3 minutes.

4. The method of claim 1, wherein the heater is a Peltier heater.

5. The method of claim 1, wherein the at least one fermentation parameter comprises at least one of a fermentation time and a fermentation temperature.

6. The method of claim 1, wherein the IR cell is an IR attenuated total reflectance (IR-ATR) cell.

7. The method of claim 1, wherein light emitted by and reflected in the IR-ATR cell may have an emitted wavelength of between about 1 micron and about 100 microns.

8. The method of claim 1, wherein the wort sample has at least one of a mass of between about 0.01 g and about 0.5 g and a volume of between about 0.01 mL and about 0.5 mL.

9. The method of claim 1, wherein the target temperature is sufficient to rapidly convert substantially all AAL in the wort sample to VDKs and carbon dioxide.

10. The method of claim 9, wherein the target temperature is between about 50° C. and about 110° C.

11. The method of claim 9, wherein the target temperature is at least about 3° C.

* * * * *